US012576120B2

(12) United States Patent
Bronfman et al.

(10) Patent No.: US 12,576,120 B2
(45) Date of Patent: Mar. 17, 2026

(54) ANTIPROLIFERATIVE EFFECT OF AGAROPHYTON CHILENSIS EXTRACT IN PROSTATE CANCER

(71) Applicants: UNIVERSIDAD ANDRES BELLO, Santiago (CL); UNIVERSIDAD SAN SEBASTIÁN, Santiago (CL)

(72) Inventors: Francisca Bronfman, Santiago (CL); Alejandro Godoy, Santiago (CL); Camila Schmidt, Santiago (CL); Loretto Contreras, Santiago (CL)

(73) Assignees: UNIVERSIDAD ANDRES BELLO, Santiago (CL); UNIVERSIDAD SAN SEBASTIÁN, Santiago (CL)

( * ) Notice: Subject to any disclaimer, the term of this patent is extended or adjusted under 35 U.S.C. 154(b) by 669 days.

(21) Appl. No.: 17/597,177

(22) PCT Filed: Jun. 28, 2019

(86) PCT No.: PCT/CL2019/050052
§ 371 (c)(1),
(2) Date: Dec. 28, 2021

(87) PCT Pub. No.: WO2020/257952
PCT Pub. Date: Dec. 30, 2020

(65) Prior Publication Data
US 2022/0305068 A1 Sep. 29, 2022

(51) Int. Cl.
| | |
|---|---|
| *A61K 36/04* | (2006.01) |
| *A61K 31/20* | (2006.01) |
| *A61K 31/201* | (2006.01) |
| *A61K 31/202* | (2006.01) |
| *A61P 35/00* | (2006.01) |

(52) U.S. Cl.
CPC .............. *A61K 36/04* (2013.01); *A61K 31/20* (2013.01); *A61K 31/201* (2013.01); *A61K 31/202* (2013.01); *A61P 35/00* (2018.01)

(58) Field of Classification Search
None
See application file for complete search history.

(56) References Cited

U.S. PATENT DOCUMENTS 9,603,881 B2 * 3/2017 Koganov ................ A61P 29/00

FOREIGN PATENT DOCUMENTS

WO WO 2014/186913 * 11/2014

OTHER PUBLICATIONS

English translation of the International Preliminary Report on Patentability issued in International Application No. PCT/CL2019/050052, Dec. 28, 2021, 7 pages.

Leighton, P., "Buscan prevenir y tratar enfermedades con alimentos, farmacos y biofilms a base de algas," El Mercurio, Jun. 29, 2018, 2 pages, available at: http://www.economiaynegocios.cl/noticias/noticias.asp?id=482711; A concise explanation of relevance provided in the International Search Report.

El Mostrador Cultura, "Investigadora chilena busca en algas la prevencion del infarto cerebral," El Mostrador, Jun. 22, 2018, 3 pages, available at: https://www.elmostrador.cl/cultura/2018/06/22/investigadora-chilena-busca-en-algas-la-prevencion-del-infarto-cerebral/; A concise explanation of relevance provided in the International Search Report.

Morales, C. et al., "Chemical composition and technological properties of red seaweed, *Agarophyton chilensis* (ex Gracilaria chilensis)," RECyT, 2019, No. 31:59-67, May 28, 2019, 9 pages; An English abstract provided on p. 1.

Honda, M. et al., "Glycerolipid Composition of the Red Macroalga Agarophyton Chilensis and Comparison to the Closely Related Agarophyton Vermiculophyllum Producing Different Types of Eicosanoids," Marine Drugs 2019, 17, 96; 11 pages.

Dewi, M. K. et al., "In vitro Evaluation of Seaweed Gracilaria verrucosa for Cytotoxic Activity against Cervical HeLa Cells," Pharmacognosy Journal, vol. 10, Issue 5, Sep.-Oct. 2018, pp. 10007-10011.

Jemasudha, T. S. et al., "Antioxidant, antibacterial, and anticancer activity from marine red algae *Gracilaria Edulis*," Asian Journal of Pharmaceutical and Clinical Research, 2019; 12(2): pp. 276-279.

Jayasree, P. et al., "Evaluation of antibacterial, antioxidant, and anticancer potentials from marine red *Algae Gracilaria* corticala," Asian Journal of Pharmaceutical and Clinical Research, 2018: 11 (7): pp. 347-350.

Shebi, S. et al., "Gracilaria foliifera (Forssk.) B0rgesen ethanolic extract triggers apoptosis via activation of p53 expression in HepG2 cells," Pharmacognosy Magazine, 2019; 15(61): pp. 259-263; available at: https://www.phcog.com/article.asp?issn=0973-1296;year-2019;volume=15;issue=61;spage=259;epage=263;aulast=Shebi.

Yeh, C-C. et al., "Antiproliferation and Induction of Apoptosis in Ca9-22 Oral Cancer Cells by Ethanolic Extract of Gracilaria tenuistipitata," Molecules, 2012; 17, pp. 10916-10927.

Elix, C. et al., "The role of peroxisome proliferator-activated receptor gamma in prostate cancer,". Asian Journal of Andrology, 2018; 20: pp. 238-243.

International Search Report and Written Opinion of PCT/CL2019/050052, Nov. 13, 2019, 12 pages including English translation of the International Search Report.

* cited by examiner

*Primary Examiner* — Vera Afremova
(74) *Attorney, Agent, or Firm* — HSML P.C.

(57) ABSTRACT

The invention relates to a pharmaceutical composition of an extract of *Agarophyton chilensis*, with antiproliferative effect in prostate cancer, comprising
(a) 0.1 to 90% of an oleoresin of *Agarophyton chilensis*, with the following major components: palmitic acid, arachidonic acid, oleic acid, stearic acid, meristic acid, linoleic acid; and
(b) 10 to 99.9% excipients and formulation aids for different pharmaceutical forms.
And its use to prepare a drug for the treatment or prevention of prostate cancer and other hyperproliferative states of prostate tissue cells.

5 Claims, 3 Drawing Sheets

ANTIPROLIFERATIVE EFFECT OF AGAROPHYTON CHILENSIS EXTRACT IN PROSTATE CANCER

TECHNICAL FIELD

The present invention corresponds to the use of an oily extract of *Agarophyton chilensis* to prepare a pharmaceutical composition with antiproliferative properties on prostate cancer cells useful for the treatment and prevention of Prostate Cancer in humans.

BACKGROUND OF THE INVENTION

Prostate cancer (CaP) is the most common type of neoplasm and represents the second leading cause of cancer death in adult men in most Western countries. This type of cancer, in its early stage, often has no symptoms or clinical signs.

The discovery and development of the prostate-specific antigen (PSA) test by Dr. T. Ming Chu's group at Roswell Park Comprehensive Cancer Center has allowed the detection of prostate cancer at earlier stages of the disease, in which the tumor is usually confined to the prostate gland or "localized" Most of these cancers are clinically indolent and can be managed conservatively. Traditional treatments for CaP located in the prostate gland include radical prostatectomy (surgical removal of the prostate) and radiation therapy. Despite this, more than 30% of patients undergoing surgical treatment resort to this treatment within a period of 5-10 years.

Once the disease has spread outside the boundaries of the prostate capsule, and has invaded adjacent tissues (advanced CaI)), standard treatment corresponds to androgen deprivation therapy (ADT). Unfortunately, most patients resort to this treatment within a period of 18 to 24 months, developing a castration-resistant tumor phenotype, which corresponds to a lethal phenotype, for which there are only palliative therapies such as chemotherapy. This background clearly demonstrates the lack of an effective therapy that allows for counteracting this disease in all its states of progression.

Until now, some preclinical studies have allowed the proposal of certain molecules as agents that prevent prostate cancer (CaP), among which are selenium, vitamin E, non-steroidal drugs and toremifene. However, clinical trials have not shown sufficient evidence to support a preventive effect of these compounds on CaP. On the other hand, clinical trials for Sa-reductase inhibitors (finasteride and dutasteride) show that these compounds do exert a preventive effect on CaP but that they also increase the risk of high-grade CaP, so their use has not yet been approved by the FDA for the treatment of this type of tumors.

In the technique there are no known extracts or natural products for the treatment or prevention of CaP. There is an extract of Berry Saw Palmetto, which has been determined to contain statins as an active compound, which has been shown to reduce blood levels of PSA, however, its role in preventing CaP is unknown, and its use is recommended for the prevention of benign prostatic hyperplasia (BPH). Another extract that is marketed for prostate diseases is based on *Pygeum africanum*, this extract has anti-inflammatory and inhibitory properties of the formation of prostaglandin PGE2 and PGF2, and its use is recommended for the treatment of BPH or prostatitis.

At the pharmacological level, there is the drug apalutamide (Erleada) which is an androgen receptor inhibitor and is used for the treatment of patients with metastatic castration-resistant CaP. There is also the drug enzalutamide (Xtandi) designed to slow the progression of CaP.

As can be seen, despite the seriousness of this disease, there are no drugs that can be used in the prevention or treatment of CaP, let alone natural extracts that fulfill this function, without important side effects.

Surprisingly, the inventors have found that the oleoresin of *Agarophyton chilensis* shows an antiproliferative effect, which has a specific action against prostate cancer cells, and is harmless on non-tumor cells. In this way, the use of *Agarophyton chilensis* extract represents an advance in the development of new products with potential capacity for prevention and/or treatment of prostate cancer, since our laboratory studies show that this extract has a significant and specific effect on the decrease in proliferation and an increase in the rate of death of highly aggressive CaP cells, not affecting the same properties in other benign human cells. So far, there are no products of this nature on the market with potential for the treatment of prostate cancer, which makes it an innovative product with great therapeutic potential.

Therefore, the present invention could have a tremendous clinical impact in counteracting this disease both in patients who present with localized tumors and in those who present with advanced disease. In addition, the invention could have a potential effect on the prevention of this disease, and probably, other pathologies associated with hyperproliferative states of prostate tissue cells such as benign prostatic hyperplasia, a pathology that affects a large percentage of adult men over 60 years of age.

This type of invention represents a novel therapy and different from the conventional therapies currently used for the treatment of prostate cancer. Therefore, they do not represent in any case a modification or variation of any type of therapy already existing for the treatment of this disease.

The group of inventors has previously developed a method of obtaining oleoresin from *Gracllaria chilensis*, which is disclosed in the application WO2014186913 (A1), which is incorporated in its entirety as a reference for the present invention. It should be noted that *Gracilaria chilensis* corresponds to an earlier name of the algae *Agorophyton chilensis*. In this first patent, it describes a method of obtaining oleoresin and its uses to activate PPARγ and participate in the recovery of pathologies in the field of diabetes, such as insulin resistance and neuropathologies such as cerebral vascular infarction. This paper does not interfere with the novelty or inventive level of the invention, as it does not anticipate anti-proliferative effects on prostate cancer cells.

DETAILED DESCRIPTION OF THE INVENTION

Figure 1:
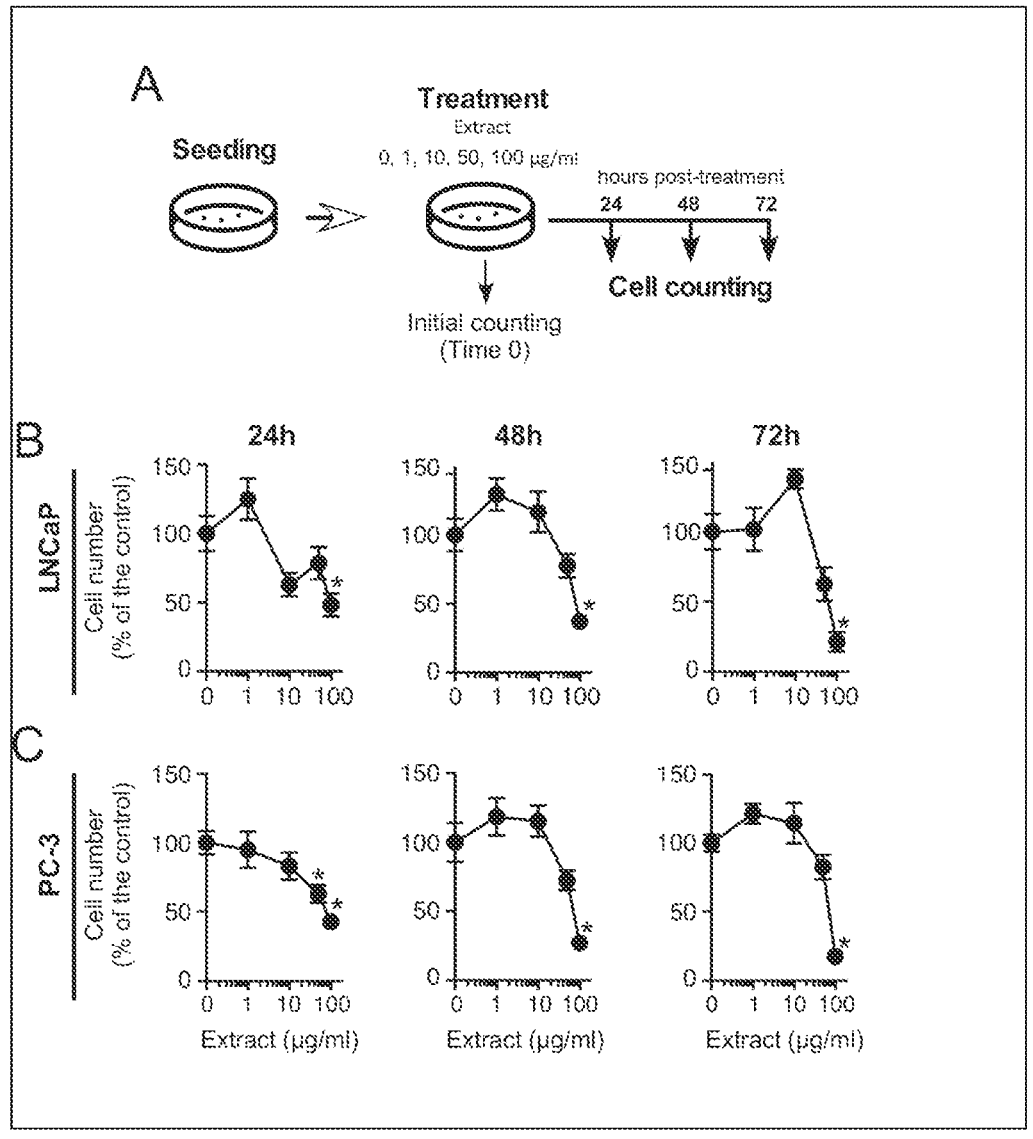
FIG. 1. Effect of oleoresin from *Agarophyton chilensis* (Extract) on the proliferation of CaP cell lines. (A) Experimental strategy to treat and count cells at 24, 48 and 72 hours incubated with increasing concentrations of the extract (0, 1, 10, 50 and 100 µg/ml), Number of cells of LNCaP (B) and PC-3 (C) cells, after 24, 48, and 72 hours (h) of incubation with oleoresin of *Agarophyton chilensis* (Extract). Each black dot represents the average of three independent experiments performed in triplicate.

The invention relates to the use of an oily extract of *Agarophyton chilensis* to prepare a pharmaceutical composition with antiproliferative properties useful for the treatment and prevention of Prostate Cancer.

In a first aspect the invention relates to a pharmaceutical composition, which includes (a) 0.1 to 90% of an oleoresin of *Agorophyton chilensis*, with the following major components: palmitic acid, arachidonic acid, oleic acid, stearic acid, myristic acid, linoleic acid; and (b) 10 to 99.9% excipients and formulation aids for different pharmaceutical forms, Where oleoresin comprises 35 to 45% palmitic acid, 14 to 25% arachidonic acid, 9 to 20% oleic acid, 2 to 8% stearic acid, 2 to 8% myristic acid and 2 to 8% linoleic acid as major components. Particularly oleoresin comprises 37 to 43% palmitic acid, 16 to 23% arachidonic acid, 11 to 18% oleic acid, 3 to 6% stearic acid, 3 to 6% myristic acid and 3 to 6% linoleic acid as major components.

This composition allows for the preparation of an antiproliferative drug useful for preventing or treating prostate cancer, either in localized tumors or in more advanced stages of the disease. As well as preventing or treating hyperproliferative states of prostate tissue cells, such as benign prostatic hyperplasia. The composition is harmless for non-tumor cells.

The drug can be formulated the form of syrups, pills, tablets, injectable solutions, gels, creams or ointments.

Another aspect the invention relates to a method of treatment and prevention of prostate cancer and other hyperproliferative states of prostate tissue cells, which consists of administering the indicated composition to individuals who suffer from or are at risk of developing prostate cancer or benign prostatic hyperplasia.

Within the excipients or auxiliaries of formulation the use of vehicles, such as mineral oil, pharmaceutical grade vegetable oil, such as soybean oil, olive, sesame, castor and preservatives, such as citric acid, methyl paraben, propyl paraben, or any other pharmaceutically acceptable vehicle or preservative available in the technique can be considered.

As indicated, the oily extract or oleoresin of *Agarophyton chilensis* is preferably obtained by the method described in patent WO2014186913, or by any other available in the technique, where the method described in said international presentation includes a liquid solid extraction, of the pulverized lyophilized algae, with dichloromethane in gaseous nitrogen atmosphere. The liquid phase of this extraction is filtered and concentrated in a rotavapor in order to eliminate the solvent, obtaining the oleoresin of *Agarophyton chilensis*.

EXAMPLES

Example 1. Preparation of the Composition

Oleoresin was obtained from the cultured and lyophilized *Agarophyton chilensis* algae, subjected to lipid extraction as described in patent application WO2014186913 (A1). 50 g of freeze-dried algae were extracted with 180 ml of dichloromethane in flasks saturated with an atmosphere of nitrogen gas and sealed, stirred at 34° C. for 30 minutes. The liquid phase was separated and a second extraction was performed under the same conditions. Both liquid phases were filtered and mixed, to undergo rotavapor drying at 39° C. for 30 minutes, to finish the evaporation of the solvent in nitrogen atmosphere. The oleoresin obtained was resuspended in a minimum volume of cyclohexane, and was lyophilized again.

The oleoresin obtained has the following composition: 51.7% saturated fatty acids, 18.2%, monounsaturated, 24.7% polyunsaturated and 2.2% trans fatty acids, the most abundant being palmitic acid, with 39%. The complete composition is shown in Table 1.

TABLE 1

| Fatty acid composition in the oleoresin of *Agarophyton chilensis* | | |
| --- | --- | --- |
| Type | Fatty acid | (%) |
| Saturated | Tridecanoic | 1.15 |
| | Myristic | 3.90 |
| | Palmitic | 39.20 |
| | Margaric | 1.30 |
| | Stearic | 4.0 |
| Polyunsaturated | Linoleic | 3.39 |
| | Arachidonic | 19.40 |
| | Alpha-linolenic | 0.61 |
| | EPA | 0.66 |
| | DHA | 0.10 |
| Monounsaturated | Oleic | 14.2 |
| Trans | — | 2.25 |

The characterization of the lipid extract or oleoresin showed that it has a high antioxidant activity, as shown in Table 2. Additionally, the presence of tocophore and carotenes was performed at the PAM Chile BC Laboratory, as well as the fatty acid profile, which is shown in Table 3.

TABLE 2

| | mg Uric Acid Eq/100 mg Extract |
|---|---|
| Total antioxidant capacity of *Agarophyton chilensis* crude extract. (Results expressed in equivalents of Uric Ac./100 mg sample) | |
| Sample | Average |
| Oily Extract of *Agarophyton chilensis* | 430 |
| Oily Extract of Spirulina | 344 |
| Oily Extract of Maqui | 305 |

These values were obtained with the Oxiselect™ Total Antioxidant Capacity (TAG) test kit from Cell Biolabs, according to the manufacturer's instructions. Oily extract from commercial samples of Maqui and Spirulina powder (n=3) is used as a comparison.

TABLE 3

| α-Tocopherol (μg/gr) | γ-Tocopherol (μg/gr) | δ-Tocopherol (μg/gr) | Total tocopherols (μg/gr) | Lycopene (μg/gr) | Beta-carotene (μg/gr) |
|---|---|---|---|---|---|
| Composition of antioxidants in crude extract (oleoresin) of *Agarophyton chilensis*. | | | | | |
| 527.7 | 5232 | 2657 | 6673 | ND | 1538 |

Determination of tocopherol content in raw extract of *Agarophyton chilensis*. The determination is expressed in micrograms of antioxidant per gram of crude extract.

Example 2. In-Vitro Effect of Extracts on Tumor Aggressiveness in Prostate Cancer Cell Lines To determine the in vitro effect of the extracts on tumor aggressiveness in prostate cancer cell lines, the following cell lines were used: LNCaP and PC-3, both prostate cancer with low and high degree of tumor aggressiveness, respectively. The cells of each line are incubated for 24 48, and 72 hours in a medium with increasing concentrations, 0, 1, 10, 50 and 100 μg/ml of the oleoresin of *Agarophyton chilensis* obtained in example 1. All experiments were performed in triplicate.

Our in vitro results in the human prostate cancer cell lines, LNCaP and PC-3, indicated that the oleoresin of *Agarophyton chilensis* inhibited, in a dose-dependent manner, the survival of both cell lines, the results are shown in FIG. 1. In these graphs, it can be interpolated that 50% inhibition, with respect to the control, would be obtained with approximately 60 μg/ml of oleoresin from *Agarophyton chilensis*. This inhibitory effect was observed in periods of time of exposure to oleoresin as short as 24 hrs and was increased in the treated cultures for longer periods (48 and 72 hours) (FIG. 1B-C).

Figure 2:
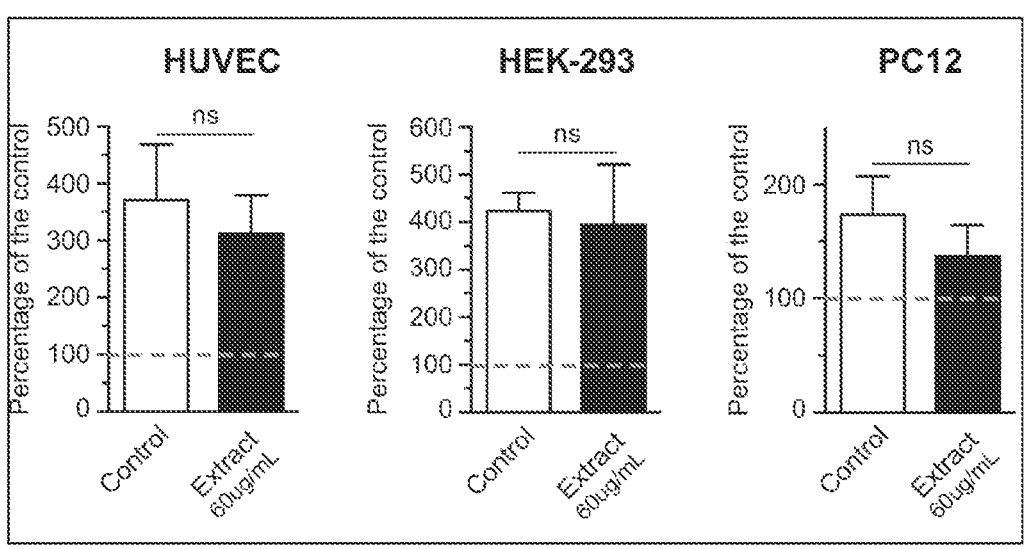
FIG. 2. Oleoresin effect of *Agarophyton chilensis* (Extract) on the proliferation of non-tumor cells. The oleoresin effect of *Agarophyton chilensis* (Extract, 60 µg/ml) on the survival of benign human HUVEC and HEK-293 cells and PC12 cells corresponding to a rat pheochromocytoma (benign tumor) at 48 hours post-treatment. The dotted line indicates the percentage of cell survival at time 0. ns: not significant with respect to the control.

Example 3. In-Vitro Effect of the Extracts on Non-Cancerous Human Cell Lines To evaluate the effect of oleoresin of *Agarophyton chilensis* on healthy tissue, the effect of mean inhibitory concentration or IC 50 (60 μg/ml) on the survival of non-malignant human cell lines such as human umbilical cord endothelial cells (HUVEC), human kidney embryonic cells (HEK-293) and pheochromocytoma (benign tumor) cells of rat adrenal medulla (PC12) was tested. The number of cells was evaluated at 48 hrs of incubation with oleoresin (treatment) The results are shown in FIG. 2. Our results showed that the oleoresin of *Agarophyton chilensis* had no significant effect on the reduction of survival in human HUVEC and HEK-293 cells, nor in cells of a benign rat tumor, PC12.

Figure 3:
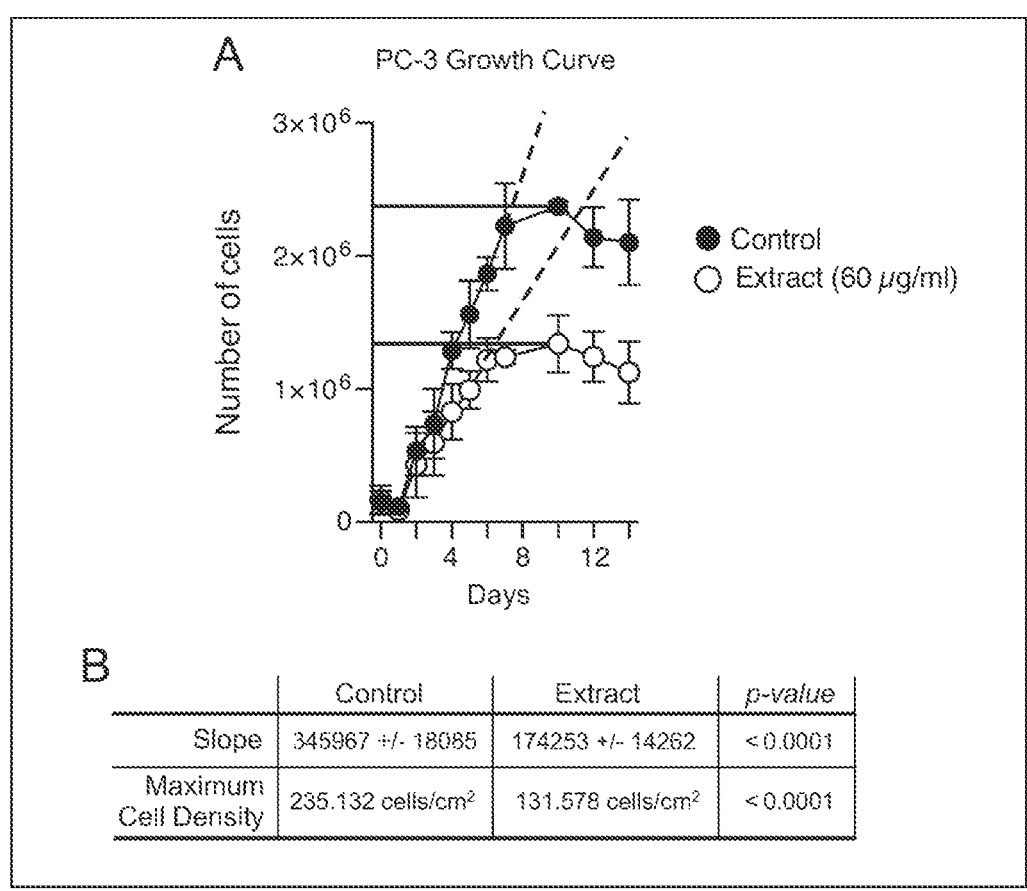
FIG. 3. Effect of oleoresin of *Agarophyton chilensis* (Extract) on the growth of CaP PC-3, (A) The number of cells was counted every day from day 1 to day 8 and every other day from day 10 to day 14, for untreated (control) cells or cells treated with *Agarophyton chilensis* oleoresin (Extract, 60 µg/ml). The black continuous horizontal lines indicate the maximum number of cells reached for each treatment (stationary phase). The dotted lines represent the changes in the slopes of each curve (exponential phase). (B) Summary table of the slopes (slope) of the exponential phase and of the maximum cell density (Maximum Cell Density) in the absence (control) and presence of oleoresin of *Agarophyton chilensis* (Extract), Each point represents two or three independent experiments performed in triplicate.

Example 4. In-Vitro Effect of Extracts on the Proliferation of Prostate Cancer Cells In order to characterize in detail the effect of the oleoresin of *Agarophyton chilensis* (60 μg/ml) on the proliferation of prostate cancer cells, the effect of the IC 50 concentration on the PC-3 prostate cancer line was evaluated, as it is highly aggressive and metastatic. A cell growth curve was performed in the absence (control) or presence of 60 μg/ml of oleoresin of *Agarophyton chilensis* for 14 days. The results are shown in FIG. 3.

Our results showed two important effects on the PC-3 cell growth curve. First, we observed a significant decrease in the slope of the exponential growth phase of the PC-3 cell growth curve in the presence of *Agarophyton chilensis* oleoresin (FIG. 3A-B), suggesting a direct inhibitory effect of *Agarophyton chilensis* on PC-3 cell proliferation.

On the other hand, a significant decrease in the stationary phase was observed in the presence of oleoresin of *Agarophyton chilensis* (60 μg/ml) compared to the control situation, which suggests a recovery of the capacity of inhibition by contact in the presence of oleoresin (FIG. 3A-B).

Figures 4, 5:
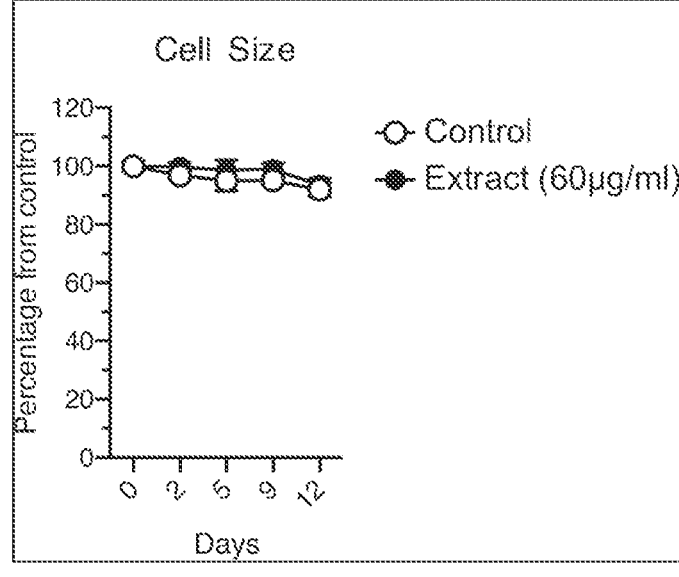
FIG. 4. Effect of Oleoresin of *Agarophyton chilensis* on cell size of the CaP PC-3 cell line. The size of PC-3 cells treated with 60 µg/ml of *Agarophyton chilensis* oleoresin (Extract) at day 2, 5, 9 and 12 of treatment Each point represents two independent experiments performed in triplicate.
FIG. 5. Effect of oleoresin of *Agarophyton chilensis* on the apoptosis of the PC-3 prostate cancer cell line. Quantification of propium iodide (PI) and annexin V staining data for untreated PC-3 cells (A) (control) or cells treated with *Agarophyton chilensis* oleoresin (B) (Extract, 60 µg/ml) for the days indicated. The black circles represent viable cells, white circles represent apoptotic cells, and white triangles represent late apoptotic cells and necrotic cells.

To confirm these latest results, changes in PC-3 cell size in the absence (control) or presence of oleoresin of *Agarophyton chilensis* (60 μg/ml) were measured at increasing incubation times, from 0 to 12 days. The results are shown in FIG. 4.

Our results showed that oleoresin of *Agarophyton chilensis* (60 μg/ml) does not significantly affect the size of PC-3 cells, which excludes the possibility that the oleoresin effect of *Agarophyton chilensis* on PC-3 cells at the stationary phase level of the growth curve is due to an increase in cell size.

Example 5. In-Vitro Effect of Extracts on Apoptosis of Prostate Cancer Cells Finally, the effect of oleoresin of *Agarophyton chilensis* (60 μg/ml) on the process of cell death (apoptosis) in PC-3 prostate cancer cells using the propidium V-Iodide annexin system was analyzed. For this, the living and dead cells in the absence and presence of oleoresin of *Agarophyton chilensis* were quantified at 2, 5, 9 and 12 days of incubation. The results are shown in FIG. 5, where the percentage of cells with respect to day 0 or control is expressed.

Our results showed that the oleoresin of *Agorophyton chilensis* significantly increased the cell death process (FIG. 5B) compared to the control condition (FIG. 5A).

Example 6. Pharmaceutical Composition

An injectable composition comprising 10% oleoresin of *Agarophyton chilensis* and 90% pharmaceutical grade castor oil was prepared.

The invention claimed is:

1. A pharmaceutical composition, comprising:
   (a) 0.1 to 90% by weight of an oleoresin of *Agarophyton chilensis* as an active ingredient, based on a total weight of the pharmaceutical composition, wherein the oleoresin of *Agarophyton chilensis* comprises 35 to 45% by weight of palmitic acid, 14 to 25% by weight of arachidonic acid, 9 to 20% by weight of oleic acid, 2 to 8% by weight of stearic acid, 2 to 8% by weight of myristic acid, and 2 to 8% by weight of linoleic acid, based on a total weight of the oleoresin of *Agarophyton chilensis*; and
   (b) 10 to 99.9% by weight of a total amount of an additional material based on the total weight of the pharmaceutical composition,
   wherein the oleoresin of *Agarophyton chilensis* further comprises docosahexaenoic acid (DHA),
   wherein the additional material comprises: a pharmaceutically acceptable excipient and formulation aid, and a pharmaceutically acceptable preservative,
   the pharmaceutically acceptable excipient and formulation aid is at least one material selected from the group consisting of mineral oil, vegetable oil, and a preservative,
   wherein the vegetable oil is at least one oil selected from the group consisting of soybean oil, olive oil, sesame oil, and castor oil, and
   the preservative is at least one material selected from citric acid, methyl paraben, and a propyl paraben, and
   wherein the pharmaceutical composition is in a form of a syrup, a pill, a tablet, an injectable solution, a gel, a cream, or an ointment.

2. The pharmaceutical composition according to claim 1, wherein the oleoresin of *Agarophyton chilensis* comprises 37 to 43% by weight of palmitic acid, 16 to 23% by weight of arachidonic acid, 11 to 18% by weight of oleic acid, 3 to 6% by weight of stearic acid, 3 to 6% by weight of myristic acid, and 3 to 6% by weight of linoleic acid, based on the total weight of the oleoresin of *Agarophyton chilensis*.

3. A method of treating prostate cancer and other hyperproliferative states of prostate tissue cells, comprising: administering an effective amount of the composition of claim 1 to a subject suffering from or being at risk of developing prostate cancer or having benign prostatic hyperplasia.

4. The pharmaceutical composition according to claim 1, comprising
   (a) 10% by weight of the oleoresin of *Agarophyton chilensis* as an active ingredient that is effective for treating prostate cancer, based on the total weight of the pharmaceutical composition, wherein the oleoresin of *Agarophyton chilensis* comprises 35 to 45% by weight of palmitic acid, 14 to 25% by weight of arachidonic acid, 9 to 20% by weight of oleic acid, 2 to 8% by weight of stearic acid, 2 to 8% by weight of myristic acid, and 2 to 8% by weight of linoleic acid, based on a total weight of the oleoresin of *Agarophyton chilensis*; and
   (b) 90% by weight as the total amount of the additional material based on the total weight of the pharmaceutical composition, wherein the additional material comprises: the pharmaceutically acceptable excipient and formulation aid, and the preservative.

5. The pharmaceutical composition according to claim 1, wherein the oleoresin of *Agarophyton chilensis* comprises the docosahexaenoic acid (DHA) in an amount of 0.1% by weight.

* * * * *